United States Patent

Peppmöller

Patent Number: 5,177,249
Date of Patent: Jan. 5, 1993

[54] COMPOUNDS WITH AT LEAST THREE FUNCTIONAL ESTER GROUPS AND PROCESS FOR THE PRODUCTION THEREOF

[75] Inventor: Reinmar Peppmöller, Krefeld, Fed. Rep. of Germany

[73] Assignee: Chemische Fabrik Stockhausen GmbH, Krefeld, Fed. Rep. of Germany

[21] Appl. No.: 623,392

[22] PCT Filed: Jun. 6, 1989

[86] PCT No.: PCT/EP89/00629
  § 371 Date: Nov. 20, 1990
  § 102(e) Date: Nov. 20, 1990

[87] PCT Pub. No.: WO89/12040
  PCT Pub. Date: Dec. 14, 1989

[30] Foreign Application Priority Data

Jun. 10, 1988 [DE] Fed. Rep. of Germany ....... 3819738

[51] Int. Cl.$^5$ .................. C07C 67/10; C07C 69/76; C07C 69/34; C07C 69/52
[52] U.S. Cl. ........................... 560/90; 560/112; 560/193; 560/199; 560/200
[58] Field of Search ............ 560/199, 193, 112, 90, 560/200; 554/148, 151, 227, 228

[56] References Cited

U.S. PATENT DOCUMENTS 3,960,935  6/1976  Samour .................. 560/199
4,316,987  2/1982  Ceprini et al. ............ 560/199

FOREIGN PATENT DOCUMENTS 1060750  3/1967  United Kingdom .

*Primary Examiner*—José G. Dees
*Assistant Examiner*—Vera C. Clarke
*Attorney, Agent, or Firm*—Sprung Horn Kramer & Woods

[57] ABSTRACT

The present invention relates to compounds comprising ester groups having at least three ester functions, to processes for the production thereof, and to the use of the products.

Compounds having at least three functional ester groups of the general formula:

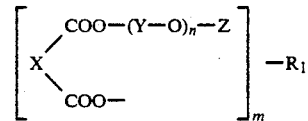

are described, wherein the abbreviations have the following meanings:
X = $-CH_2-CH_2-$ or $-CH=CH-$,
Y = bivalent, saturated aliphatic hydrocarbon residue optionally substituted,
Z = optionally substituted acyl residue $-CO-R$
$R_1$ = the residue of an alcohol, or a group from an alkylene-oxide-adduct taking the alcohol function in the ester grouping.
n = 1 to 3 and
m = 1 to 3.

9 Claims, No Drawings

COMPOUNDS WITH AT LEAST THREE FUNCTIONAL ESTER GROUPS AND PROCESS FOR THE PRODUCTION THEREOF

The present invention relates to compounds comprising ester groups having at least three ester functions, to a process for the production thereof, and to the use of the products.

Monoesters of dicarboxylic acids are known. If these compounds are tried to be condensed with diols or polyols, polycondensates are formed and it is impossible to obtain low-molecular compounds by a reaction which may technically be utilized.

British Patent No. 1,379,335 describes the attempt to produce emulsion stabilizers by the reaction of unsaturated glycidyl esters with dicarboxylic acid monoesters. Owing to the tendency towards rearrangement and to the temperature sensitivity of the products obtained, the tedious reaction leads to polymer-containing and/or instable end products which do not permit technical utilization from the economic point of view.

The same applies to the alkoxylation of succinic acid with ethylene oxide where a bis-(hydroxy-ethyl)-succinate tending to rearrange is obtained (German Patent No. 544 288).

Proceeding from this state of the art, it is the object of the present invention to provide stable compounds comprising several ester functions starting from dicarboxylic acid monoesters, and it is a further object of the present invention to provide a process for the production of these compounds.

This object is achieved by the synthesis of ester-groups-containing-compounds having at least three functional ester groups of the following general formula; in the following these are called "triesters" according to the denotation $m=1$.

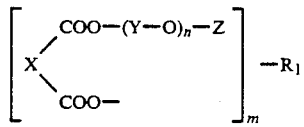

The abbreviations have the following meaning:
$x = -CH_2-CH_2-$ or $-CH=CH-$,
$Y =$ bivalent, saturated aliphatic hydrocarbon residue optionally substituted with one or more etherified or esterified hydroxy groups,
$Z =$ acyl residue—$CO-R$ of a monobasic or dibasic, saturated or unsaturated aliphatic, cycloaliphatic or aromatic carboxylic acid with 2 to 22 carbon atoms, optionally with a saturated or unsaturated $C_4$-$C_{16}$-hydrocarbon residue as substituent,
$R_1 =$ the residue of a monovalent or multivalent saturated or unsaturated aliphatic, cycloaliphatic or aromatic alcohol, or a group from an alkylene-oxide-adduct taking the alcohol function in the ester grouping,
$n = 1$ to 3
$m = 1$ to 3.

Two synthesis methods were found.

The first one comprises the reaction of a dicarboxylic acid monoester with an epoxide, i.e., an alkoxylation of the carboxylic acid group whereby the dicarboxylic acid monoester-alkoxylate (dicarboxylic acid-hydroxyalkyl-alkyl-diester) resulting as intermediate product and being thermally instable is subsequently acylated and thus converted into the form of a stable triester.

The dicarboxylic acid monoester-alkoxylates resulting as intermediate product have the general formula:

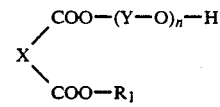

in which x, Y, $R_1$, n, and m have the above mentioned meanings.

The acylation of the hydroxyalkyl group of the intermediate product, which hydroxyalkyl group tends to continue condensating, results in the formation of the temperature-resistant triesters. Acylation is carried out at temperatures ranging from 50° to 120° C., preferably 60° to 90° C., and can be applied to nearly all hydroxyalkyl-alkyl-dicarboxylic acid mixed esters.

In case of immediate conversion of the epoxide-addition-products into the thermally stable triesters by way of acylation, higher reaction temperatures and thus higher and more efficient reaction rates become possible.

The addition of the epoxide to the carboxyl function of the monoester is possible without catalyst, however, to increase the reaction velocity acidic or basic catalysts are generally used (Houben-Weyl, 4th edition, 6/3, page 447 ff.).

Longer residence of the formed intermediate product at elevated temperatures favors rearrangements. For this reason, addition of several moles alkylene oxide to the dicarboxylic acid monoester is limited due to the required longer reaction time. According to the present invention 1 to 3 moles are added.

A residual amount of unreacted dicarboxylic acid monoester in the reaction mixture after alkoxylation has a stabilizing influence on the formed hydroxyalkyl-alkyl-mixed ester. Preferably the acid value of the alkoxylation mixture is at least 5; in case of values below 5 considerable variations in pressure and rearrangement reactions occur.

If 1 to 3 moles alkylene oxide are added, the acid value preferably amounts to at least 10.

Compared to the dicarboxylic acid monoester, the hydroxyalkyl-alkyl-dicarboxylic acid esters so manufactured have a lower melting point and a lower water-solubility, particularly in the neutral to subalkaline range. This frequently permits a purification of the hydroxyalkyl ester with water or an aqueous salt solution.

Longer storage periods of the hydroxyalkyl esters is possible preferably at temperatures below 0° C., even if they are washed out and free of catalysts. Further purification of the intermediate product by thermal processes, such as fractional distillation, result in undesired polymer products and cleavage of alcohol and glycols. Therefore, the intermediate product is preferably immediately subjected to further treatment.

The dicarboxylic acids used for the production of the dicarboxylic acid monoesters serving as starting product may be aliphatic, saturated or unsaturated acids.

Important representatives of the dicarboxylic acids are succinic acid, maleic acid and fumaric acid.

Anhydride forming acids are preferred, since the production of the monoesters is effected most easily from the anhydrides of the dicarboxylic acid.

Any mono- or multivalent saturated or unsaturated primary, secondary, or tertiary alcohols may be employed as alcohol component for the formation of the dicarboxylic acid monoester.

Important representatives are: methanol, ethanol, propanol, butanol, pentanol, hexanol, heptanol, octanol, nonanol, decanol, undecanol, dodecanol, eicosanol, cetyl alcohol, myricyl alcohol, ethylene glycol, propylene glycol, butylene glycol, hexylene glycol, glycerol, trimethylolpropane, sorbitol, sorbitan, diethylene glycol, polyethylene glycol, dipropylene glycol, polypropylene glycol, ethylene glycol monomethyl ether, diethylene glycol monomethyl ether, polyethylene glycol capped at one end, polypropylene glycol closed at one end, polyrandom-adducts of ethylene and propylene oxide, fatty alcohol oxethylates, fatty alcohol propoxylates, nonylphenol oxethylates, nonylphenol propoxylates, allyl alcohol, cinnamyl alcohol, and benzyl alcohol.

In principle, all alkylene oxide adducts containing acidic hydrocarbon are suitable too.

The quantity ratios between alcohol and dicarboxylic acid or dicarboxylic anhydride, respectively, are chosen according to the stoichiometric reaction to the semi-ester. In case of multivalent alcohols, partial esterifications are possible too. The reaction is carried out at temperatures below 120° C., preferably below 90° C., however, the temperature may be elevated to up to this value for a short time, if the melting point of the anhydride is above this temperature. If low-boiling alcohols or sublimating substances are used, the reaction is carried out in a pressure vessel. Due to their thermo-instability, the produced monoesters are suitably directly further processed, when they are in hot state.

All compounds having epoxide structure may be used to form the hydroxyalkyl esters. Preferred representatives of this group of epoxides are: ethylene oxide, propylene oxide, 1,2-epoxibutane, 2,3-epoxi-1-propanol, glycidyl acrylate, glycidyl methacrylate, glycidyl allyl ether, 1,3-butanediene monooxide, styrene oxide, epoxiethyl butyrate, 1,2-epoxicyclodeca-5,9-diene, 1,2-epoxicyclododecan, 1,2-epoxicyclohexane, exo-2,3-epoxinorbornene, 2,3-epoxipropyl-4-methoxiphenyl ether.

A sterically and/or kinetically unfavorable selection of the reactants may lead to an interference of the reaction rates and/or yields.

According to the present invention the thermally stable triesters are obtained by the reaction of the thermolabile intermediate product with an acylating agent. Preferably carboxylic anhydrides, carboxylic acid chlorides or ketenes are used for the acylation. Acylation is carried out subsequent to the epoxide addition to the dicarboxylic acid monoester at the same temperature.

Transesterifications or polymer formations, respectively, are prevented by the acylation of the OH-groups.

Compared to the alcohol residue of the dicarboxylic acid mono-ester, kind and length of the hydrocarbon residue in the acylating agent have a greater influence on the physical properties of the mixed ester. For example, the acetyl-oxiethyl-benzyl maleinate is a low-viscosity, waterwhite liquid at room temperature, whereas the benzoyl-oxyethyl-methylmaleate is rearranged to the fumaric acid ester under distillation conditions and forms a white crystallizate below 51° C.

According to an embodiment of the process according to the present invention, a reaction of the hydroxyalkyl-alkyl-ester with dicarboxylic acid anhydrides is carried out similar to the above described formation of the monoesters.

In case of this synthesis modification the triester-molecule obtained exhibits both the structure of a dicarboxylic acid-diester and that of a dicarboxylic acid-monoester. In this connection, the same or even different dicarboxylic acid parent substances may be combined in one molecule. The carboxylic acid anhydrides are selected according to the same criteria as described for the production of the dicarboxylic acid monoester.

The triesters may be directly synthesized by the reaction of dicarboxylic acid monoester with alkylene carbonates, such as ethylene carbonate (1,3-dioxolan-2-one) or propylene carbonate (4-methyl-1,3-dioxolan-2-one), respectively, in the presence of an acylating agent.

In case of this synthesis method, the stage of the thermolabile intermediate product, the hydroxyalkyl-alkyl-dicarboxylic acid diester, is skipped. The elevated reaction temperatures of above 120° C., which then become possible, on the one hand permit higher reactions velocities and, on the other hand, the direct removal by distillation of the released monocarboxylic acid, if low-boiling anhydrides are used as acylating agent, for example, acetic anhydride. This method is particularly suitable for the production of small triester quantities, and for the reaction of dicarboxylic acid monoesters having high melting points. In the latter case, hydroxyalkylation with an epoxide would result in rearrangements and polyester formation.

The processes according to the present invention are particularly preferred for alkoxylates.

The triesters according to the present invention— which are thermally stable and resistant to storage—exhibit advantageous properties with respect to consistency, odour, boiling point, and flash point, connected with an adjustable oil and water compatibility.

Due to the presence of at least three functional ester groups and to the possibility of varying at least three structural elements of the triesters according to the present invention, a plurality of possible compounds according to the teaching of the present invention result. They are suitable as solvents or solubilizers, respectively, as softeners, antistatics, and lubricants. The sulfited triesters of unsaturated carboxylic acid exhibit wetting agent properties. In general, the products are well biodegradable and thus are not harmful to the environment.

Due to the incorporation of unsaturated carboxylic acids and subsequent sulfitation, a wide selection of low-pollution surfactants is provided; their field of application ranges from hydrophobing agents up to wetting agents or detergents, respectively.

By the incorporation of unsaturated groups, for example, esterification with an unsaturated alcohol, such as allyl alcohol with a dicarboxylic acid, or by acylation with an unsaturated carboxylic acid, such as acrylic acid, polymer units are formed which can emphasize the above mentioned advantages, for example, as permeate plasticizers in polymerized form within a polymeric substance.

The thermostability of the triesters according to the present invention is such high that vacuum distillation—even at high temperatures—is possible without decomposition so that the obtained triester can be purified over a fractionating column. However, if unsaturated triesters, such as the maleinates, are distilled, the formation of isomers, such as the fumarates, must be expected at higher temperatures, approximately starting from 150° C. These isomers can scarcely be separated by distillation. A complete conversion is effected in case of distilling stearoyl-, oxiethyl-, and methyl maleate (cf. Example 9).

Identification and characterization of the liquid triesters distilled under high vacuum can be carried out, amongst others, by determination of density d, refractive index n, and molar mass M.

The following esters according to the present invention were manufactured:

1) Acetyl-oxiethyl-methyl maleate
2) Acetyl-oxipropyl-methyl maleate
3) Acetyl-oxiethyl-ethyl maleate
4) Acetyl-oxiethyl-2-ethylhexyl maleate
5) Acetyl-oxiethyl-benzyl maleate
6) Acetyl-oxiethyl-methyl succinate
7) Acetyl-oxiethyl-ethyl succinate
8) Acetyl-oxiethyl-n-propyl succinate
16) Acetyl-oxiethyl-allyl maleate.

TABLE 1

| Example | Dicarboxylic acid component | Alcohol | Epoxide | Acylating component | Boiling point | Density g/ml | Refractive index n (20° C.) |
|---|---|---|---|---|---|---|---|
| 1. | MA | methanol | EO | AcA | 102° C./0.1 bar | 1.19 | 1.455 |
| 2. | MA | methanol | PO | AcA | 105° C./0.1 bar | 1.16 | 1.453 |
| 3. | MA | ethanol | EO | AcA | 103° C./0.1 bar | 1.16 | 1.454 |
| 4. | MA | 2-ethyl-hexanol | EO | AcA | 126–128° C. (0.1 bar) | 1.04 | 1.455 |
| 5. | MA | benzyl-alcohol | EO | AcA | 148° C./0.1 bar | 1.17 | 1.439 |
| 6. | SA | methanol | EO | AcA | 102° C./0.1 bar | 1.17 | 1.439 |
| 7. | SA | ethanol | EO | AcA | 103° C./0.1 bar | 1.13 | 1.441 |
| 8. | SA | n-propanol | EC | AcA | 103° C./0.1 bar | 1.11 | 1.440 |
| 9. | MA | methanol | EO | stear. | 220° C./0.3 bar | melting point: | 61° C. |
| 10. | MA | methanol | EO | benz. | 147° C./0.25 bar | melting point: | 51° C. |
| 12. | MA | diglycol | EO | AcA | saponification value: 547 | | |
| 13. | MA | PEG 600 | EO | AcA | saponification value: 331 | | |
| 14. | MA | n-octa-decanol | EO | n-octenyl-succinic anhydride | saponification value: 85 | | |
| 15. | MA | dto. | EO | isododecenyl-succinic anhydride | saponification value: 78 | | |
| 16. | MA | allyl alcohol | EO | AcA | 106° C./0.15 bar | 1.16 | 1.465 |

According to the Lorentz-Lorentz equation $$R_M = \frac{n^2 - 1}{n^2 + 2} \times \frac{M}{d}$$

there is a relation to the molar refraction ($R_M$) which is a characteristic value and can be calculated from the atomic or bond refraction, respectively, ("increments") (J. Chem. Soc. 1948, pages 1804 to 1855, and Römpps Chemie-Lexikon, 8th edition, vol. 5, page 3534). This requirement is fulfilled for the primary products, i.e., pure triesters with the epoxide-addition-number n=1.

General preparation instruction for Examples 1 to 8 and 16:

1 mol dicarboxylic acid monoester, produced from equimolar quantities of dicarboxylic anhydride and alcohol at 70° C., is heated under nitrogen in the autoclave at 80° C. with 1.5 mol of an epoxide in the presence of 0.5 to 1.0%-wt dimethyl benzylamine as catalyst. After a reaction period of 1 hour, the acid value drops to a value below 15.1 to 1.5 ml carboxylic anhydride are added to the reaction product, and it is then again stirred for another hour at 80° C. Subsequently, the content of the reaction vessel is distilled under high-vacuum over a fractionating column.

Table 1 shows a survey of the crude products used and of the boiling points of the obtained triesters, as well as the densities and refractive indexes at 20° C. Further fractions are obtained at temperatures above the indicated boiling temperatures (higher by approximately 20° to 30° C.). These fractions result from a multiple-addition of the epoxide to the dicarboxylic acid monoester.

Abbreviations: MA=maleic anhydride; SA=succinic anhydride; EO=ethylene oxide; PO=propylene oxide; EC=ethylene carbonate; AcA=acetic anhydride; stear.=stearoyl chloride; benz.=benzyl chloride; PEG 600=polyethylene glycol of molar mass 600.

EXAMPLE 1

Acetyl-oxiethyl-methyl maleate: 780 g maleic acid monomethyl ester, prepared from 588 g maleic anhydride and 192 g methanol at 70° C., were heated to 80° C. under nitrogen in the autoclave together with 396 g ethylene oxide in the presence of 10 g dimethyl benzylamine. After a reaction period of 1 hour, the acid value had dropped to 16 (0.28 mmol/g). 700 g acetic anhydride were added to the reaction product and it was stirred for one further hour at 80° C. Subsequently, the content of the reaction vessel was distilled under high-vacuum over a fractionating column.

The product converted at 102° C. (0.1 mbar) and at 20° C. was an inodorous, low-viscosity liquid having a density of 1.19 g/ml and a refractive index of 1.455.

A further fraction was obtained at 125° to 130° C. (0.1 mbar). This was the acetylated diethylene glycol ester with moieties of the triethylene glycol ester of the monomethyl maleate.

EXAMPLE 2

Acetyl-oxipropyl-methyl maleate: In accordance with Example 1, 780 g maleic acid monomethyl ester were reacted with 504 g 1,2-epoxipropane in the presence of 10 g dimethyl benzylamine and subsequently with 700 g acetic anhydride. Then the reaction mixture was subjected to fractionation.

The product had a boiling point of 105° C. (0.1 mbar) and a density of 1.16 g/ml and a refractive index of 1.453 at 20° C.

A further fraction was obtained between 125° and 130° C. (0.1 mbar) which consisted of the acetylated dipropylene glycol ester with portions of the tripropylene glycol ester of the monomethyl maleate.

EXAMPLE 3

Acetyl-oxiethyl-ethyl maleate: 864 g maleic acid monoethyl ester, produced from 588 g maleic anhydride and 276 g ethanol at 70° C., were heated to 80° C. in the autoclave under nitrogen with 396 ethylene oxide in the presence of 10 g dimethyl benzylamine. After a reaction period of 1 hour, 700 g acetic anhydride were added and then stirred at 80° C. for 1 hour.

The product was subsequently fractionated and had a boiling point of 103° C. (0.1 mbar) and was an inodorous, low-viscosity, water-white liquid at 20° C. having a density of 1.16 g/ml and a refractive index of 1.454.

A second fraction was obtained at 125° to 130° C. and consisted of the acetylated diethylene glycol- and tri-ethylene glycol ester of the monoethyl maleate.

EXAMPLE 4

Acetyl-oxiethyl-ethylhexyl-maleate: 1824 g maleic acid-mono-2-ethylhexyl ester, prepared from 784 g maleic anhydride and 1040 g 2-ethylhexanol, were reacted at 80° C. with 528 g ethylene oxide in the presence of 20 g dimethyl benzylamine and subsequently with 900 g acetic anhydride.

Distillation of the reaction mixture over a fractionating column resulted in a product having a boiling point of 126° to 128° C. (0.1 mbar). At 20° C. the density amounted to 1.04 g/ml and the refractive index was 1.455. The triester was an inodorous, low-viscosity liquid.

A second fraction was obtained between 135° and 138° C. and consisted of the acetylated diethylene- and tri-ethylene glycol ester of the monomethyl maleate.

EXAMPLE 5

Acetyl-oxiethyl-benzyl maleate: 824 g maleic acid-monobenzyl ester, prepared from 392 g maleic anhydride and 432 g benzyl alcohol, were reacted at 80° C. with 264 g ethylene oxide in the presence of 10 g dimethyl benzylamine and subsequently with 450 g acetic anhydride. After acylation of the oxethylate, the triester was distilled under vacuum over a fractionating column.

The compound had a boiling point of 148° C. at 0.1 mbar. It had a density at 20° C. of 1.19 g/ml and a refractive index of 1.511. It was an inodorous, low-viscosity, waterwhite liquid.

The distillate taken above 160° C. mainly contained the acetylated diethylene glycol ester and triethylene glycol ester of the monobenzyl maleate/fumarate.

EXAMPLE 6

Acetyl-oxiethyl-methyl succinate: 792 g succinic acid monomethyl ester, prepared from 600 g succinic anhydride and 192 g methanol, were reacted at 80° C. with 396 g ethylene oxide in the presence of 10 g dimethyl benzylamine and subsequently with 700 g acetic anhydride. After acylation, the reaction mixture was subjected to high-vacuum distillation.

The compound was obtained at 102° C. (0.1 mbar) and was an inodorous, low-viscosity, water-white liquid at 20° C. It had a density of 1.17 g/ml and a refractive index of 1.439.

A second fraction consisting of the acetylated diethylene glycol ester and triethylene glycol ester of the monomethyl succinate was obtained at 125° to 130° C.

EXAMPLE 7

Acetyl-oxiethyl-ethyl succinate: 876 g succinic acid monoethyl ester, produced from 600 g succinic anhydride and 276 g ethanol, were reacted at 80° C. with 396 g ethylene oxide under nitrogen in the autoclave in the presence of 10 g dimethyl benzylamine and subsequently with 700 g acetic anhydride at the same temperature. After acetylation, the reaction mixture was distilled under high-vacuum.

The compound had a boiling point of 103° C. at 0.1 mbar and was an inodorous, low-viscosity, waterwhite liquid at 20° C. It had a density of 1.13 g/ml and a refractive index of 1.441.

A further fraction was obtained at 130° to 135° C. It consisted of the acetylated diethylene glycol- and tri-ethylene glycol ester of the monoethyl succinate.

EXAMPLE 8

Acetyl-oxiethyl-n-propyl succinate: 160 g succinic acid mono-n-propyl ester, prepared from 100 g succinic anhydride and 60 g n-propanol, were heated to the boil with 90 g ethylene carbonate and 140 g acetic anhydride with connected fractionating column. Starting from 140° C., the mixture reacted under formation of acetic acid which was withdrawn at the top of the column. The temperature was slowly elevated to 200° C. and maintained at this temperature for another hour. Then it was cooled down to approximately 50° C. and vacuum distillation started.

The compound had a boiling point of 103° to 104° C. at 0.1 mbar. At 20° C. it was an inodorous, waterwhite, low-viscosity liquid having a density of 1.11 g/ml and a refractive index of 1.440.

A further fraction was obtained in the boiling range of 140° to 160° C., and it consisted of the acetylated diethylene glycol ester and triethylene glycol ester of the mono-n-propyl succinate.

EXAMPLE 9

Stearoyl-oxiethyl-methyl fumarate: 390 g maleic acid monomethyl ester (see Example 1) were reacted at 80° C. in the autoclave under nitrogen with 198 g ethylene oxide in the presence of 5 g dimethyl benzylamine and subsequently treated with 910 g stearoyl chloride at the same temperature. The reaction product was distilled under high vacuum, whereby the compound converted at 220° C. (0.3 mbar) and was maintained above its melting point in the cooler. After recrystallization in acetone, a melting point of 61° C. resulted for the compound. Appearance and consistency of the substance were similar to a hard wax.

EXAMPLE 10

Benzoyl-oxiethyl-methyl fumarate: 780 g maleic acid monomethyl ester (see Example 1) were reacted with 396 g ethylene oxide in the presence of 10 g dimethyl benzylamine at 80° C. in the autoclave under nitrogen and subsequently treated with 845 g benzoyl chloride at the same temperature for 1 hour. Then the triester was distilled under high vacuum over a fractionating column and maintained above its melting point in the cooling device.

The compound had a boiling point of 147° C. at 0.25 mbar. After recrystallization in acetone, white needles having a melting point of 51° C. were obtained.

EXAMPLE 12

Bis-acetoxiethyl-maleic-acid-diethylene-glycol-ester: 1224 g bis-maleic-acid-diethylene-glycol-monoester, prepared from 636 g diethylene glycol and 588 g maleic anhydride at 70° C., were reacted with 396 g ethylene oxide in the presence of 10 g dimethyl benzylamine in the autoclave under nitrogen at 80° C., and subsequently acylated with 700 g acetic anhydride. The reaction mixture was then poured into approximately 2 l of cold water, firmly shaken and the aqueous phase discarded. A saponification value of 547 was determined for the water-insoluble triester.

EXAMPLE 13

Bis-acetoxiethyl-maleic-acid-polyethylene-glycol (600)-ester: 1592 g bismaleic acid-polyethylene-glycol (600)-monoester, prepared from 1200 g polyethylene glycol (OH-number: 187) and 392 g maleic anhydride, were reacted in the autoclave under nitrogen at 80° C. with 198 g ethylene oxide in the presence of 10 g dimethyl benzylamine and subsequently acylated with 600 g acetic anhydride. The reaction mixture was then poured into approximately 2 l of warm water (appr. 60° C.) and firmly shaken. After sedimentation, the aqueous phase was discarded and the residual oil dried. The polyglycol ester had a saponification value of 331 and a turbidity point of approximately 53° C.

EXAMPLE 14 n-octenyl-succinoyl-oxiethyl-octadecyl-maleate: 1083 g n-octadecyl-maleate, prepared from 789 g Alfol 16/20 (tradename to Messrs. Condea, FRG, for a fatty alcohol $C_{16-20}$) and 294 g maleic anhydride, were reacted with 145 g ethylene oxide in the presence of 10 g dimethyl benzylamine at 80° C. in the autoclave under nitrogen and then aftertreated with 630 g n-octenyl-succinic anhydride for 1 hour at the same temperature. Subsequently, the reaction product was firmly shaken with water (approximately 50° C.), separated and dried. It resulted a bright-yellow oil with an ester number of 4.99 mmol/g and an acid value of 85. A water-soluble gel spontaneously formed with alkali or ammonia.

EXAMPLE 15

Isododecenyl-succinoyl-oxiethyl-octadecyl-maleate: As described in Example 12, 1228 g oxethylated octadecyl maleate were reacted with 795 g isododecenyl succinic anhydride. After purification with warm water and drying, a yellow oil with an ester number of 4.30 mmol/g and an acid value of 78 was obtained. On addition of alkali or ammonia the product was water-soluble under formation of gel.

EXAMPLE 16

Acetyl-oxiethyl-allyl maleate: 936 g maleic acid monoally ester, prepared from 588 g maleic anhydride and 348 g allyl alcohol, were reacted with 396 g ethylene oxide in the presence of 10 g dimethyl benzylamine and subsequently with 750 g acetic anhydride. The reaction mixture was subsequently subjected to a fractionation under vacuum. 500 ppm phenothiazole were used for stabilization purposes.

The compound had a boiling point of 106° C. at 0.15 mbar and exhibited a density of 1.16 g/ml and a refractive index of 1.465 at 20° C. It was water-white, highly liquid and almost inodorous.

A second fraction was obtained between 120° and 130° C. It was the acylated diethylene glycol ester and tri-ethylene glycol ester of the monoallyl maleate.

It is understood that the specification and examples are illustrative but not limitative of the present invention and that other embodiments within the spirit and scope of the invention will suggest themselves to those skilled in the art.

I claim:

1. A compound with at least three functional ester groups of the formula:

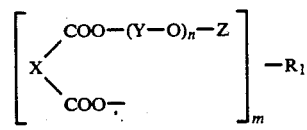

in which the abbreviations have the following meaning:
X = —$CH_2$—$CH_2$— or —CH=CH—,
Y = bivalent, saturated aliphatic alcohol hydrocarbon or substituted with one or more etherified or esterified hydroxy groups,
Z = acyl —CO—R of a monobasic or dibasic, saturated or unsaturated aliphatic, cycloaliphatic or aromatic carboxylic acid with 2 to 22 carbon atoms, which carboxylic acid is unsubstituted or substituted with a saturated or unsaturated $C_4$-$C_{16}$-hydrocarbon group,
$R_1$ = a monovalent or multivalent saturated or unsaturated aliphatic alcohol group, cycloaliphatic or aromatic alcohol group, or a group from an alkylene-oxide-adduct taking the alcohol function in the ester grouping,
n = 1 to 3
m = 1 to 3.

2. A compound according to claim 1 wherein Y represents a saturated grouping formed by the addition of alkylene- or cycloalkylene oxide, or one or more etherified or esterified hydroxy groups.

3. A process for the production of a compound as defined in claim 1, wherein a dicarboxylic acid monoester is reacted with an epoxide and the intermediate stage of the hydroxyalkyl-alkyl-dicarboxylic acid diester is acylated.

4. A process according to claim 3 wherein the reaction of the dicarboxylic acid monoester with the epoxide is carried out at temperatures between 50° and 120° C.

5. A process according to claim 4 wherein the reaction of the dicarboxylic acid monoester with the epoxide is carried out at temperatures between 60° and 90° C.

6. A process for the production of a compound as defined in claim 1, wherein a dicarboxylic acid monoester is reacted with an alkylene carbonate in the presence of an acylating agent.

7. A process according to claim 6 wherein the reaction is carried out at temperatures above 120° C.

8. A process according to any one of claims 3 to 7 wherein a dicarboxylic acid anhydride is used as acylating agent.

9. A process according to claims 3, 4 or 5, wherein acylation of the intermediate product is carried out with an acid chloride, acid anhydride or ketene.

* * * * *

UNITED STATES PATENT AND TRADEMARK OFFICE
CERTIFICATE OF CORRECTION

PATENT NO. : 5,177,249

DATED : January 5, 1993

INVENTOR(S) : Reinmar Peppmoller

It is certified that error appears in the above-identified patent and that said Letters Patent is hereby corrected as shown below:

Col. 10, line 24   After " aliphatic " delete " alcohol "

Signed and Sealed this

Twenty-fourth Day of May, 1994

*Attest:*

BRUCE LEHMAN

*Attesting Officer*      Commissioner of Patents and Trademarks